United States Patent
Damm et al.

(10) Patent No.: US 6,667,028 B2
(45) Date of Patent: Dec. 23, 2003

(54) HAIR GROWTH PROMOTER

(75) Inventors: Peter Damm, Olpe (DE); Friedrich Noser, Bonnefontaine (CH); Rainer Schweickert, Griesheim (DE); Hans Heinrich, Viernheim (DE); Eva Reinemund, Hirschberg (DE)

(73) Assignee: Wella Aktiengesellschaft, Darmstadt (DE)

( * ) Notice: Subject to any disclaimer, the term of this patent is extended or adjusted under 35 U.S.C. 154(b) by 0 days.

(21) Appl. No.: 10/159,310

(22) Filed: May 31, 2002

(65) Prior Publication Data

US 2003/0031639 A1 Feb. 13, 2003

Related U.S. Application Data

(62) Division of application No. 09/744,892, filed as application No. PCT/EP99/06269 on Aug. 26, 1999, now Pat. No. 6,488,922.

(30) Foreign Application Priority Data

Oct. 1, 1998 (DE) .......................... 198 45 202

(51) Int. Cl.$^7$ ..................... A61K 7/06; A61K 31/505; A61K 31/44

(52) U.S. Cl. ................. 424/70.1; 424/401; 514/256; 514/272; 514/275; 514/277; 514/345; 514/880

(58) Field of Search .................. 424/70.1, 401; 514/256, 272, 275, 277, 345, 880

(56) References Cited

U.S. PATENT DOCUMENTS 5,466,694 A * 11/1995 Terranova et al. .......... 514/272

FOREIGN PATENT DOCUMENTS

WO       WO 86/00616 A1 *  1/1986

* cited by examiner

Primary Examiner—Michael G. Hartley
Assistant Examiner—Marina Lamm
(74) Attorney, Agent, or Firm—Michael J. Striker

(57) ABSTRACT

The method for promoting hair growth and/or reducing hair loss includes providing a certain agent for reducing hair loss and/or promoting hair growth, applying an effective amount of the agent to hair and scalp, after applying the agent massaging the scalp for one to five minutes and leaving the agent on the hair and the scalp for at least 24 hours. The agent includes a compound of the formulae (I), (II) and/or (III):

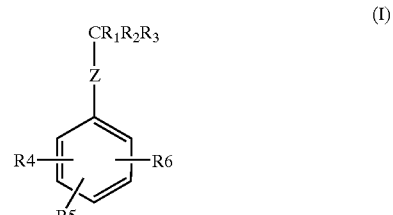

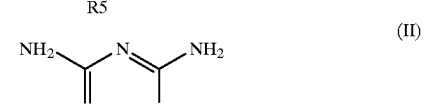

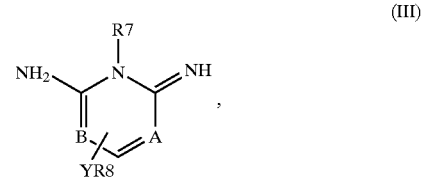

or a physiologically compatible salt or salts thereof, as effective ingredient.

8 Claims, No Drawings

HAIR GROWTH PROMOTER

CROSS-REFERENCE

This is a divisional of U.S. patent application Ser. No. 09/744,892, filed Jan. 31, 2001, now U.S. Pat. No. 6,488,922, which is a 371 of PCT/EP99/06269, filed Aug. 26, 1999.

BACKGROUND OF THE INVENTION

1. Field of the Invention

The present invention relates to a method of promoting hair growth and/or decreasing hair fall-out using certain cyclic compounds.

2. Description of the Related Art

The human scalp normally harbors 100,000 to 150,000 hair follicles or hairs. The hair follicles or hair roots or hair bulbi are the hair-forming organs. The long, strong hairs, which build up the hair coverage of the head, are referred to as terminal hairs. The very fine, very short hairs, barely protruding over the surface of the skin, at the edges of the hair coverage on the head, are referred to as fuzz hair, or as vellus hair. The growth of hair is not continuous, but cyclical. Three growth phases are identified: (1) the anagen, during which the hair grows, (2) the katagen, during which the hair follicle prepares for the next phase, the telogen, and the previously growing hair is converted into a resting hair or club hair and (3) the telogen, that is, the resting phase during which hair growth ceases completely. In response to a signal, which is not identified at the present time, the telogen follicle awakens to a new activity or commences a new anagen, in the course of which a new hair grows and the existing club hair is shed. This hair growth cycle proceeds unchanged during the whole life and, moreover equally in the case of the long, strong terminal hair as well as in the case of the very short fuzz hair of vellus hair. A prerequisite for a normal growth of a healthy head of hair is a perfectly functioning organism and an optimum supply for it of all the necessary nutrients and auxiliary materials. Many factors can affect the growth of the hair on the head, namely wrong nutrition, deficient nutrition, severe illnesses, medicinal drugs, emotional stresses and temporary disorders of the hormone balance in the organism. A loss of hair, brought about by such factors, usually is temporary.

SUMMARY OF THE INVENTION

It is therefore an object of the present invention to provide method of promoting hair growth and/or reducing hair loss by applying certain cyclic compounds.

According to the invention this method comprises the steps of:
a) providing an agent comprising at least one of a compound of formula (I), a compound of formula (II) and a compound of formula (III) and a physiologically compatible salt thereof:

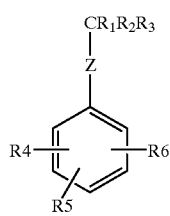
(I)

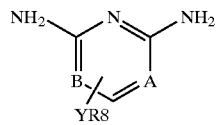
(II)

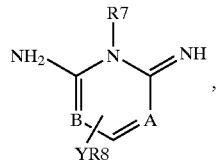
(III)

wherein A and B, independently of each other, are each a CH group or a nitrogen atom, with the proviso that at least one of A and B is the CH group; Y represents —O—, —(CH$_2$)$_n$—, —NH—CH$_2$—, —CH$_2$—NH—, —N=N—, —CH=CH, —CH$_2$—O—, —O—CH$_2$, —N=CH—, —CH=N, —(CH$_2$—CH$_2$—O)$_m$— or —(O—CH$_2$—CH$_2$)$_m$—, with m and n, independently of each other, equal to 1, 2, 3 or 4;

Z represents —NH—CH$_2$—, —CH$_2$—CH$_2$—, —CH=CH— or —CH$_2$—NH—;

R1 represents —H, —OH or a hydroxyalkyl group having one to four carbon atoms;

R2 represents —H, a cyclopropyl group or an alkyl group containing from one to four carbon atoms;

R3 represents a hydroxyalkyl group having one to two carbon atoms, —CH$_2$—X or —CHX$_2$, —COCH$_3$, —CF$_3$, —CH$_3$ or

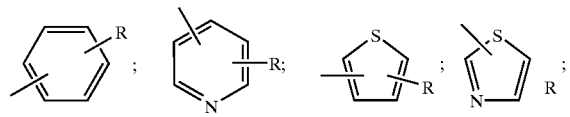

wherein X represents F, Cl, Br or I and R represents —NO$_2$, —SO$_2$CH$_3$, —CF$_3$, —CHF$_2$, —CH$_2$F, —F or —Cl;

R4, R5 and R6, independently of each other, each represent —NO$_2$, —CF$_3$, —CHF$_2$, —CH$_2$F, —F, —Cl, —Br or —H;

R7 represents —OH, —OSO$_3$H, —OALK or —OCOCH$_3$, wherein ALK represents an alkyl group having one to four carbon atoms;

R8 represents an alkyl group with one to six carbon atoms, a hydroxyalkyl group having from one to six carbon atoms, a hydroxyalkenyl group having from two to six carbon atoms, an aryl group, a heteroaryl group or an alkenyl carboxylic acid group having two to six carbon atoms;

with the proviso that, when R4 is at a 2 position and represents —NO$_2$ in the compound of formula (I), R5 is in a 4 position and represents —CF$_3$, R6 represents —H and ZCR1R2R3 represents —NH—CH=CH—CHOH—CH$_2$OH;

b) applying the agent to hair and scalp in an amount sufficient for promoting of hair growth and/or decreasing hair loss; and c) leaving the agent on the hair and scalp for a predetermined time interval.

Preferred compounds of formula (I) for use as the agent in the method of the invention are those in which Z is —NH—CH$_2$—, —CH$_2$—CH$_2$—, —cH=CH— or —CH$_2$—NH—, R1 is —OH, —CH$_2$OH or —CH$_2$CH$_2$OH, R2 is —H, —CH$_3$ or —C$_2$H$_5$; and R3 represents

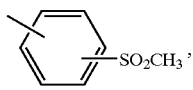

a hydroxyalkyl group containing from one to two carbon atoms, —CH$_2$F, —CH$_2$CL, —CH$_2$Br, —CH$_2$I, —CF$_3$ or —CH$_3$, and R4, R5 and R6 are each, independently of each other, —NO$_2$, —CF$_3$, —CHF$_2$, —CH$_2$F, —F, —Cl, —Br or —H. However the compounds of formula (I) are particularly preferred, in which R1 is —H or —CH$_2$OH, R2 is —H or —CH$_3$, R3 is a hydroxyalkyl group with one to two carbon atoms, —CH$_2$F, —CH$_2$cl, —CH$_2$Br, —CH$_2$I, —CF$_3$ or —CH$_3$, and R4 represents —NO$_2$, R5 represents —CF$_3$ and R6 represents —H. The compounds of formula (I) are especially particularly preferred in which Z represents —NH—CH$_2$—, R1 represents —OH, R2 represents —H, R3 represents —CH$_2$OH, R4 represents —NO$_2$, R5 represents —CF$_3$ and R6 represents —H.

Preferred compounds of formula (II) for use as the agent in the method of the invention are those in which the A represents the OH group, B represents the CH group or a nitrogen atom, Y represents —N=N—, —(CH$_2$)$_n$—,— CH=CH—, —N=OH— or —CH=N—, and R8 represents an alkyl group with one to six carbon atoms, a hydroxyalkyl group having from one to six carbon atoms, a phenyl group, a benzyl group or a pyridyl group. However compounds of formula (II) are especially preferred, in which A and B both represent a —CH— group, Y represents —N=N— and R8 represents a pyridyl group.

Preferred compounds of formula (III) for use as the agent in the method of the invention are those in which V represents —N=N—, —(CH$_2$)$_n$—, —CH=CH—, —N=CH— or ——CH=N—; R7 represents —OH, —OSO$_3$H or —OALK, wherein ALK is the alkyl group having one to four carbon atoms and R8 represents an alkyl group with one to six carbon atoms, a hydroxyalkyl group having from one to six carbon atoms, a phenyl group, a benzyl group or a pyridyl group. Compounds of formula (III) which are especially preferred are those in which Y represents —N=N—, R7 represents —OH (including the corresponding tautomeric N-oxides) and R8 represents a pyridyl group.

The following exemplary compounds are preferred for use as the agent in the method of the invention: 1-[N-(2'-nitro-4'-trifluoro-methylphenyl)amino]-3-chloro-2-hydroxypropane, 1-[N-(2'-nitro-4'-trifluoro-methylphenyl) amino]-2-hydroxy-2-trifluoromethylethane, 1-[N-(2'-nitro-4'-trifluoro-methylphenyl)-amino]-propan-2,3-diol, 1-(2'-nitro-4'-trifluoro-methylphenyl)-1-butene-3,4-diol, 2,6-diamino-3-((pyridin-3-yl)-azo)pyridine and 2,6-diamino-3-((pyridin-3-yl)-azo)pyridin-1-oxide. Of these exemplary compounds 1-[N-(2'-nitro-4'-trifluoro-methyl-phenyl)amino]-2,3-propylene glycol and 2,6-diamino-3-((pyridin-3-yl)azo)pyridine and combinations thereof are particularly preferred.

The cosmetic agent according to the invention may be in any form suitable for application to hair and scalp, especially in the form of an aqueous, alcoholic or aqueous-alcoholic preparation, such as a solution, gel, cream, emulsion or dispersion. It is also possible to dispense this agent as a spray or a foam from a pressurized container with conventional blowing agents, which are liquefied under pressure, for example, chlorofluoroalkanes, such as CCl$_3$F, CCl$_2$F$_2$, C$_2$Cl$_3$F$_3$, CCl$_2$F$_2$, CHCl$_2$F$_2$ and (CClF$_2$)$_2$, highly volatile hydrocarbons, such as n-butane, and n-propane, or also dimethyl ether, carbon dioxide, nitrous oxide, nitrogen, methylene chloride and 1,1,1-trichloromethane.

The forms, in which the inventive cosmetic agents are prepared, may also remain on the hair and the scalp and comprise, for example, insertion materials, combing gels, hair pomades, hair oils and hair treatments. Especially preferred are the hair treatments as well as so-called "sustained release" preparations, which emit the active ingredient uniformly over a longer period of time, or the producing of the compounds of formulae (I) and (II) as liposomes.

The total content of compounds of formula (1) and/or (II) in the inventive agent preferably is about 0.001 to 10 percent by weight, an amount of 0.05 to 3 percent by weight being particularly preferred.

The composition of the inventive cosmetic agent represents a mixture of the compounds of formulas (I) and/or (II) with components, which are customary for such agents, such as carriers and additives.

As carriers, in general those materials come into consideration, which increase the percutaneous absorption of the active ingredients, do not disadvantageously affect the active ingredient components and, at the same time, are harmless with respect to the human skin. Such carrier materials are, for example, water, low molecular weight aliphatic alcohols, such as ethanol, propanol and isopropanol, as well as mixtures of these materials. However, mixtures of the aforementioned compounds with 1 to 30 percent by weight of 1,2-propylene glycol are also advantageous.

The following come into consideration as conventional additives in the inventive cosmetic agents: carrier compounds or penetration accelerators, such as benzyl alcohol, 2-benzyl-oxyethanol, α-hydroxycarboxylate esters, vanillin, p-hydroxyanisole, 3-hydroxy-4-methoxy-benzaldehyde, 2-phenoxyethanol, salicylaldehyde, 3,5-dihydroxybenzaldehyde, 3,4-dihydroxybenzaldehyde, 4-hydroxy-phenylacetamide, methyl p-hydroxybenzoate, p-hydroxy-benzaldehyde, m-cresol, hydroquinone monomethyl ether, o-fluorophenol, m-fluorophenol, p-fluorophenol-2-(2'-hydroxyphenoxy)-ethanol, 3,4-methylene-dioxyphenol, resorcinol monomethyl ether, 3,4-dimethoxyphenol, 3-trifluoromethyl-phenol, resorcinol monoacetate, ethylvanillin, 2-thiophenethanol, butyl lactate and butyl glycolate; thickeners, such as kaolin, bentonite, fatty acids, higher fatty alcohols, starch, polyacrylic acid, cellulose derivatives, alginates, Vaseline or paraffin oil; compounds from the classes of the anionic, cationic, amphoteric, zwitterionic or nonionic surfactants or surface active agents, such as fatty alcohol sulfates, alkyl sulfonates, alkylbenzene sulfates, quaternary ammonium salts, alkyl betaines and ethoxylated esters of fatty acids; furthermore, opacifiers, such as polyethylene glycol esters, foam stabilizers, sequestering agents, buffers, preservatives, solubilizers, perfume oils, natural or synthetic cosmetic polymers, such as cellulose derivatives, shellac, pectins, polyvinylpyrrolidone, polyvinyl acetate, polyacrylic compounds, such as acrylic acid or methacrylic acid polymers, basic polymers of esters of acrylic acid or methacrylic acid with aminealcohols, polyacrylonitrile and chitosan derivatives, hair conditioners, active ingredients against dandruff, plant extracts as well as hair-care components, such as protein hydrolysates, lanolin derivatives, cholesterol, pantothenic acid or betaine.

Of course, the inventive agents may contain additional, known active ingredients, which maintain a healthy growth of hair and/or support or promote the recuperation of hair growth in the case of disorders of a physiological or non-physiological kind, such as Minoxidil, diazoxide, cyclosporin A, diphenylhydantoin, acetazolamide, antiandrogens of a steroidal and nonsteroidal type, such as cyproterone acetate, oxendolone, spirolactone, 5-alpha-reductase inhibitors, selected extracts of natural origin, retinoids, estrogens, vitamins, such as biotin, trace elements, neuropeptides, nutrients, especially of the essential type, cytokins, neurotrophins, neutrophin receptor antagonists, antimicrobial substances, steroidal or non-steroidal anti-inflammatory substances, calcium antagonists or potassium channel openers (potassium channel agonists).

The present invention furthermore relates to a method for treating hair to reduce hair fall-out and promote hair growth, wherein a sufficient amount of the previously described inventive agent, containing at least one compound of formula (I) or (II), in general about 1 to 30 milliliter and preferably 2 to 15 milliliter, is applied on the hair and scalp, the scalp is massaged subsequently preferably for about 1 to 5 minutes, and the agent is left on the hair and the scalp for prolonged period of time, preferably for at least 24 hours.

Preferably, the treatment is carried out once or twice daily and for a period of 3 to 24 months. Optionally, the interval between applications can then be increased.

A further object of the present invention is the use of compounds of formulas (I), (II) and/or (III), alone or in combination with one another, to promote hair growth and/or to decrease androgenic loss of hair. The use of one or more compounds from the group consisting of 1-(N-(2'-nitro-4'-trifluoromethyl-phenyl)-amino)-3-chloro-2-hydroxy-propane, 1-(N-(2'-nitro-4'-trifluoromethyl-phenyl)-amino)-2-hydroxy-2-trifluoromethylethane, 1-(N-(2'-nitro-4'-trifluoromethyl-phenyl)-amino)-2,3-propylene glycol, 1-(2'-nitro-4'-trifluoro-methyl-phenyl)-3,4-dihydroxy-1-butene, 2,6-diamino-3-((pyridine-3-yl)-azo)-pyridine and 2,6-diamino-3-((pyridine-3-yl)-azo)-pyridine-1-oxide. Of these compounds, especially 1-(N-(2'-nitro-4'-trifluoromethyl-phenyl)-amino)-2,3-propylene glycol and 2,6-diamino-3-((pyridine-3-yl)-azo)-pyridine is particularly preferred for promoting hair growth and/or decreasing androgenic loss of hair.

The invention is explained in greater detail by means of the following examples, without being limited to these.

EXAMPLES

Example 1

Hair Tonic

| | |
|---|---|
| 1.0 g | 1-(N-(2'-nitro-4'-trifluoromethyl-phenyl)-amino)-2,3-propylene glycol |
| 1.0 g | 2,6 diamino-3-((pyridine-3-yl)-azo)-pyridine |
| 3.0 g | 1,2-propylene glycol |
| 0.3 g | perfume oil |
| to 100.0 g | ethanol (96%) |

In each case, 15 milliliters of the above hair tonic are applied once daily (every 24 hours) on the hair and the scalp and massaged into the scalp for 1 minute.

Example 2

Hair Tonic

| | |
|---|---|
| 2.0 g | 1-(N-(2'-nitro-4'-trifluoromethyl-phenyl)-amino)-2,3-propylene glycol |
| 1.0 g | 2,6 diamino-3-((pyridine-3-yl)-azo)-pyridine |
| 0.1 g | menthol |
| 0.3 g | perfume oil |
| to 100.0 g | ethanol (96%) |

The above hair tonic is applied twice daily on the hair and the scalp and massaged into the scalp for 2 minutes.

Example 3

Hair Tonic

| | |
|---|---|
| 0.30 g | 1-(N-(2'-nitro-4'-trifluoromethyl-phenyl)-amino)-2,3-propylene glycol |
| 0.05 g | polyvinylpyrrolidone |
| 0.10 g | Arnika tincture |
| 0.30 g | perfume oil |
| to 100.00 g | ethanol (96%) |

The above hair tonic (in each case 10 milliliters) is applied twice daily on the hair and the scalp and massaged into the scalp for 2 minutes.

Example 4

Hair Tonic

| | |
|---|---|
| 1.0 g | 1-(N-(2'-nitro-4'-trifluoromethyl-phenyl)-amino)-2,3-propylene glycol |
| 0.5 g | 2,6 diamino-3-((pyridine-3-yl)-azo)-pyridine |
| 0.2 g | hydrogenated castor oil with 60 moles of ethylene oxide (Chremophor RH 60 of BASF AG/Ludwigshafen |
| 0.3 g | perfume oil |
| 40.0 g | ethanol (96%) |
| to 100.0 g | water |

The above hair tonic (in each case 20 milliliters) is applied once daily on the hair and the scalp and massaged into the scalp for 1 to 2 minutes.

Example 5

Hair Treatment

| | |
|---|---|
| 0.4 g | 1-(N-(2'-nitro-4'-trifluoromethyl-phenyl)-amino)-2,3-propylene glycol |
| 0.2 g | hydrogenated castor oil with 60 moles of ethylene oxide (Chremophor RH 60 of BASF AG/Ludwigshafen |
| 0.3 g | perfume oil |
| 0.5 g | cetyl alcohol |
| to 100.0 g | water |

The above hair treatment (in each case 15 milliliters) is applied once daily on the hair and the scalp and massaged into the scalp for 2 minutes. After a period of action of about 24 hours, the hair treatment is rinsed out with lukewarm water.

Example 6

Hair Tonic

| | |
|---|---|
| 1.0 g | 1-(N-(2'-nitro-4'-trifluoromethyl-phenyl)-amino)-3-chloro-2-hydroxy-propane |
| 1.0 g | 2,6 diamino-3-((pyridine-3-yl)-azo)-pyridine |
| 3.0 g | 1,2-propylene glycol |
| 0.3 g | perfume oil |
| to 100.0 g | ethanol (96%) |

In each case, 15 milliliters of the above hair tonic are applied once daily (every 24 hours) on the hair and the scalp and massaged into the scalp for 1 minute.

Example 7

Hair Tonic

| | |
|---|---|
| 2.0 g | 1-(N-(2'-nitro-4'-trifluoromethyl-phenyl)-amino)-2-hydroxy-2-trifluoro-methylethane |
| 1.0 g | 2,6 diamino-3-((pyridine-3-yl)-azo)-pyridine |
| 0.1 g | menthol |
| 0.3 g | perfume oil |
| to 100.0 g | ethanol (96%) |

The above hair tonic is applied twice daily on the hair and the scalp and massaged into the scalp for 2 minutes.

Example 8

Hair Tonic

| | |
|---|---|
| 0.30 g | 1-(N-(2'-nitro-4'-trifluoromethyl-phenyl)-amino)-1-butene-3,4-diol |
| 0.05 g | polyvinylpyrrolidone |
| 0.10 g | Arnika tincture |
| 0.3 g | perfume oil |
| to 100.0 g | ethanol (96%) |

The above hair tonic (in each case 10 milliliters) is applied twice daily on the hair and the scalp and massaged into the scalp for 2 minute.

Example 9

Hair Tonic

| | |
|---|---|
| 0.7 g | 1-(N-(2'-nitro-4'-trifluoromethyl-phenyl)-amino)-2,3-propylene glycol |
| 0.9 g | 2,6 diamino-3-((pyridine-3-yl)-azo)-pyridine-1-oxide |
| 0.2 g | hydrogenated castor oil with 60 moles of ethylene oxide (Chremophor RH 60 of BASF AG/Ludwigshafen |
| 0.3 g | perfume oil |
| 50.0 g | ethanol (96%) |
| to 100.0 g | water |

The above hair tonic (in each case 20 milliliters) is applied once daily on the hair and the scalp and massaged into the scalp for 1 to 2 minute.

Example 10

Hair Treatment

| | |
|---|---|
| 0.3 g | 1-(N-(2'-nitro-4'-trifluoromethyl-phenyl)-amino)-2,3-propylene glycol |
| 0.01 g | 2,6 diamino-3-((pyridine-3-yl)-azo)-pyridine-1-oxide |
| 0.2 g | hydrogenated castor oil with 60 moles of ethylene oxide (Chremophor RH 60 of BASF AG/Ludwigshafen |
| 0.3 g | perfume oil |
| 0.5 g | cetyl alcohol |
| to 100.0 g | ethanol (96%) |

The above hair treatment (in each case 15 milliliters) is applied once daily on the hair and the scalp and massaged into the scalp for 2 minutes. After a period of action of about 24 hours, the hair treatment is rinsed out with lukewarm water.

Example 11

Hair Growth Emulsion

| | |
|---|---|
| 0.4 g | 1-(N-(2'-nitro-4'-trifluoromethyl-phenyl)-amino)-2,3-propylene glycol |
| 0.1 g | 2,6 diamino-3-((pyridine-3-yl)-azo)-pyridine |
| 30.0 g | partially hydrogenated peanut oil (oleum arachidis hydrogenatum) |
| 5.0 g | cetyl stearyl alcohol |
| 0.2 g | perfume oil |
| 10.0 g | propylene glycol |
| to 100.0 g | water |

The above hair growth agent (in each case 20 milliliters) is applied once daily on the hair and the scalp and massaged into the scalp for 1 to 2 minute. After a period of action of about 24 hours, the agent is rinsed out with lukewarm water.

Example 12

Hair Growth Gel

| | |
|---|---|
| 0.300 g | 1-(N-(2'-nitro-4'-trifluoromethyl-phenyl)-amino)-2,3-propylene glycol |
| 0.560 g | carboxyvinyl polymer (Carbopol 940 of BF Goodrich/USA) |
| 0.224 g | sodium hydroxide |
| to 100.000 g | water |

The above hair growth agent (in each case 15 milliliters) is applied once daily on the hair and the scalp and massaged into the scalp for 2 minutes. After a period of action of about 24 hours, the agent is rinsed out with lukewarm water.

Unless it is stated otherwise, all weight data is given as weight percent.

What is claimed is:

1. A method of at least one of promoting hair growth and decreasing hair loss, said method comprising the steps of:

a) providing an agent comprising at least one member selected from the group consisting of compounds of formula (II), and physiologically compatible salts thereof;

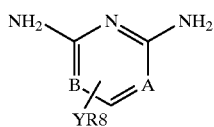

(II)

wherein A and B, independently of each other, are each a CH group or a nitrogen atom, with the proviso that at least one of said A and B is said CH group;

Y represents —O—, —(CH$_2$)$_n$—, —NH—CH$_2$—, —CH$_2$—NH—, —N=N—, —CH=CH—, —CH$_2$—O—, —O—CH$_2$—, —N=CH—, —CH=N—, —(CH$_2$—CH$_2$—O)$_m$— or —(O—CH$_2$—CH$_2$)$_m$—, with m and n, independently of each other, equal to 1, 2, 3 or 4;

R8 represents an alkyl group with one to eight carbon atoms, a hydroxyalkyl group having from one to six carbon atoms, a hydroxyalkenyl group having from two to six carbon atoms, an aryl group, a heteroaryl group or an alkenyl carboxylic acid group having two to six carbon atoms; and b) applying said agent to hair and scalp in an amount sufficient for said promoting of said hair growth or said decreasing of said hair loss; and c) leaving said agent on said hair and scalp for a predetermined time interval.

2. The method as defined in claim 1, wherein said predetermined time interval is at least 24 hours.

3. The method as defined in claim 1, wherein after said applying said scalp is massaged for another predetermined time interval.

4. The method as defined in claim 3, wherein said another predetermined time interval is for from 1 to 5 minutes.

5. A method of at least one of promoting hair growth and decreasing hair loss, said method comprising the steps of:
a) providing an agent comprising at least one member selected from the group consisting of compounds of formula (II), compounds of formula (III) and physiologically compatible salts thereof;

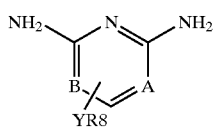

(II)

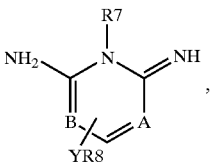

(III)

wherein A and B, independently of each other, are each a CH group or a nitrogen atom, with the proviso that at least one of said A and B is said CH group;

wherein Y represents —O—, —(CH$_2$)$_n$—, —NH—CH$_2$—, —CH$_2$—NH—, —N=N—, —CH=CH—, —CH$_2$—O—, —O—CH$_2$—, —N=CH—, —CH=N—, —(CH$_2$—CH$_2$—O)$_m$— or —(O—CH$_2$—CH$_2$)$_m$—, with m and n, independently of each other, equal to 1, 2, 3 or 4;

wherein R7 represents —OH, —OSO$_3$H, —OALK or —OCOCH$_3$, wherein ALK represents an alkyl group having one to four carbon atoms;

wherein R8 represents an alkyl group with one to eight carbon atoms, a hydroxyalkyl group having from one to six carbon atoms, a hydroxyalkenyl group having from two to six carbon atoms, an aryl group, a heteroaryl group or an alkenyl carboxylic acid group having two to six carbon atoms; and b) applying said agent to hair and scalp in an amount sufficient for said promoting of said hair growth or said decreasing of said hair loss; and c) leaving said agent on said hair and scalp for a predetermined time interval;

wherein said agent comprises said compound of the formula (II) in which A represents said CH group and B represents said CH group, Y represents said —N=N—, said —(CH$_2$)$_n$—, said —CH=CH—, said —N=CH— or said —CH=N—, and R8 represents said alkyl group with one to six carbon atoms, said hydroxyalkyl group having from one to six carbon atoms, a phenyl group, a benzyl group or a pyridyl group.

6. A method of at least one of promoting hair growth and decreasing hair loss, said method comprising the steps of;
a) providing an agent consisting of 2,6-diamino-3-((pyridin-3-yl)azo)pyridine;
b) applying said agent to hair and scalp in an amount sufficient for said promoting of said hair growth or said decreasing of said hair loss; and
c) leaving said agent on said hair and scalp for a predetermined time interval.

7. The method as defined in claim 1, wherein said agent is a hair tonic or a preparation for sustained release of said agent.

8. A method of at least one of promoting hair growth and decreasing hair loss, said method comprising the steps of:
a) providing an agent comprising at least one member selected from the group consisting of compounds of formula (II) and physiologically compatible salts thereof;

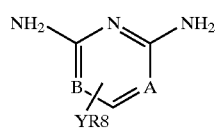

(II)

wherein A and B, independently of each other, are each a CH group or a nitrogen atom, with the proviso that at least one of said A and B is said CH group;

Y represents —O—, —(CH$_2$)$_n$—, —NH—CH$_2$—, —CH$_2$—NH—, —N=N—, —CH=CH—, —CH$_2$—O—, —O—CH$_2$—, —N=CH—, —CH=N—, —(CH$_2$—CH$_2$O)$_m$— or —(O—CH$_2$CH$_2$)$_m$—, with m and n, independently of each other, equal to 1, 2, 3 or 4;

R8 represents an alkyl group with one to six carbon atoms, a hydroxyalkyl group having from one to six carbon atoms, a hydroxyalkenyl group having from two to six carbon atoms, an aryl group, a heteroaryl group or an alkenyl carboxylic acid group having two to six carbon atoms; and b) applying said agent to hair and scalp in an amount sufficient for said promoting of said hair growth or said decreasing of said hair loss;

c) massaging said scalp for one to five minutes after the applying of step b); and d) leaving said agent on said hair and said scalp for at least 24 hours.

* * * * *